US00PP16031P3

(12) United States Plant Patent
Jensen et al.

(10) Patent No.: US PP16,031 P3
(45) Date of Patent: Oct. 11, 2005

(54) *CAMPANULA* PLANT NAMED 'PKMP02'

(50) Latin Name: *Campanula portenschlagiana*
Varietal Denomination: PKMp02

(75) Inventors: Gert Kim Jensen, Odense N (DK); Per Elmegaard Andersen, Skalskor (DK)

(73) Assignees: Gartneriet PKM ApS, Odense N (DK); Gartneriet Elmegaard Andersen, Skalskor (DK)

( * ) Notice: Subject to any disclaimer, the term of this patent is extended or adjusted under 35 U.S.C. 154(b) by 21 days.

(21) Appl. No.: 10/648,303

(22) Filed: Aug. 27, 2003

(65) Prior Publication Data

US 2004/0244083 P1 Dec. 2, 2004

(30) Foreign Application Priority Data

May 26, 2003 (QZ) ..... PBR20030981

(51) Int. Cl.[7] ..... A01H 5/00
(52) U.S. Cl. ..... Plt./263
(58) Field of Search ..... Plt./263

(56) References Cited

PUBLICATIONS

UPOV hits on 'PKMp02', Plant Variety Database 2004/02, UPOV–rom, GTI–Jouve Retrieval Software.*

* cited by examiner

*Primary Examiner*—Anne Marie Grunberg
(74) *Attorney, Agent, or Firm*—Foley & Lardner, LLP

(57) ABSTRACT

A new and distinct cultivar of *Campanula* plant named 'PKMp02', characterized by having compact, upright plant habit; dense and bushy plant form mainly due to more upright stems; vigorous growth habit and no need for chemical growth retardation; greater number of flowers per plant, large upright blue flowers, and no need for vernalization.

4 Drawing Sheets

Latin name of genus and species of the plant claimed: *Campanula portenschlagiana.*
Variety denimination: 'PKMp02'.

BACKGROUND OF THE INVENTION

The present Invention relates to a new and distinct cultivar of *Campanula* plant, botanically known as *Campanula portenschlagiana* Schult., commonly known as Dalmatian Bellflower, and hereinafter referred to by the name 'PKMp02'.

The new *Campanula*, 'PKMp02', is a product of a planned breeding program conducted by the Inventors, Gert K. Jensen and Per Elmegaard Andersen, in Søhus, Denmark. The new *Campanula* originated from a cross made in 2001 by the Inventors between a proprietary selection of *Campanula portenschlagiana* Schult named '08.08' (unpatented) as the female parent and a proprietary selection of *Campanula portenschlagiana* Schult named '08.98.05' (unpatented) as the male parent. The Inventors selected the new *Campanula* cultivar from the progeny of the above cross in 2001 on the basis of its compact and freely flowering habit. Plants of the new *Campanula* are more upright, compact and more freely flowering than plants of both parental selections.

Asexual reproduction of the new cultivar by terminal cuttings taken and propagated in Søhus, Denmark, has shown that the unique features of this new *Campanula* are stable and reproduce true to type in many successive generations.

SUMMARY OF THE INVENTION

Plants of the cultivar 'PKMp01' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'PKMp02'. These characteristics in combination distinguish 'PKMp02' as a new and distinct cultivar:

1. Upright plant habit;
2. Dense and bushy plant form, mainly due to more upright stems;
3. Vigorous growth habit, and less need for chemical growth retardation;
4. Large upright blue flowers;
5. Greater number of flowers per plant; and
6. No need for vernalization.

Side-by-side comparisons between the instant plant and the parental cultivars, '08.08' and '08.98.05', were conducted by the Inventors in Stige, Denmark. Plants of 'PKMp02' differ from the cultivars '08.08. and 08.98.05' in the following characteristics:

1. Plants of 'PKMp02' have shorter internodes and shorter leaves and more upright growth than plants of the cultivars '08.08' and '08.98.05'.
2. Plants of 'PKMp02' have light gray-green colored leaves with pubescence whereas plants of the cultivars '08.08' and '08.98.05' have green-colored leaves.
3. Plants of 'PKMp02' have shorter flower peduncles than plants of the cultivars '08.08' and '08.98.05'.
4. Plants of 'PKMp02' are shorter and more compact than the plants of the cultivars '08.08' and '08.98.05'.
5. Plants of 'PKMp02' have more flowers per plant and larger flowers than the plants of the cultivars '08.08' and '08.98.05'.

Of the many commercial cultivars known to the inventor, the most similar in comparison to 'PKMp02' are the *Campanula portenschlagiana* Schult. parental cultivars '08.08' and '08.98.08'.

BRIEF DESCRIPTION OF THE DRAWINGS

The accompanying photographic drawings illustrate the overall appearance of the new cultivar, showing the colors as true as it is reasonably possible to obtain in colored reproductions of this type. Colors in the photographs may differ slightly from the color values cited in the detailed botanical description, which more accurately describe the actual colors of 'PKMp02'.

The first photograph shows a side perspective view of a typical flowering plant of 'PKMp02' as grown in a 11 cm pot.

The second photograph drawing shows a top perspective view of a typical flowering plant of 'PKMp02' (referenced '08.01.13') as grown.

The third photograph shows close-up view of a typical flower of 'PKMp02' (reference '08.01.13') compared to a close-up view of a typical flower of the female parental cultivae, '08.08'.

The fourth photograph shows an top perspective view showing both buds and flowers of a typical plant of 'PKMp02'..

DETAILED BOTANICAL DESCRIPTION

In the following description, color references are made to The Royal Horticultural Society (R.H.S.) Colour Chart, $4^{th}$ edition. Plants were grown under greenhouse conditions. The plants described were about 14 weeks old after cutting, as grown in 10.5 cm pots.

Parentage:
- *Female parent.*—Proprietary selection of *Campanula portenschlagiana* Schult named '08.08'.
- *Male parent.*—Proprietary selection of *Campanula portenschlagiana* Schult named '08.98.05'.

Propagation:
- *Type cutting.*—Terminal vegetative cuttings.
- *Time to initiate roots.*—About 10 to 14 days at 18 to 21° C. in tunnels in a greenhouse.
- *Root description.*—Fine, well branched.

Plant description:
- *Form.*—Perennial, herbaceous plant with upright plant habit, and overall globular shape. *Campanulate* flowers in racemes. Freely branching with lateral branches forming at every node; dense and bushy.
- *Crop time.*—After rooting, about 14 weeks are required to produce finished flowering plants in 11 cm pots.
- *Plant height* (*soil level to top of plant plane*).—About 15 cm.
- *Plant spread.*—23–27 cm.
- *Lateral branches.*—Approximately 65–75, average length 11–13 cm, average branch diameter 1–2 mm; 5–7 leaves per lateral branch.
- *Internode length.*—15 mm.
- *Stem.*—RHS 143B in color.
- *Vigor.*—Vigorous growth rate.

Foliage description: Leaves single, dentate, cordate, palmate venation.
- *Length.*— 15–20 mm.
- *Width.*—About 25 mm.
- *Shape.*—Cordate.
- *Apex.*—Acuminate.
- *Base.*—Cordate.
- *Margin.*—Broadly dentate.
- *Texture.*—Smooth, glabrous, dull. Short stiff hairs on abaxial side and along veins and margin.
- *Color.*—Young foliage, upper and lower surfaces: 137A, green. Mature foliage, upper and lower surfaces: N138B and 137B respectively. Venation color 138A, palmate venation pattern.
- *Petiole.*—4–6 cm in length, 1–2 mm in diameter, RHS N138D in color.

Flower description:
- *Flower number per plant.*—1500–2000.
- *Flower arrangement and shape.*—Upright, single flowers in racemes; *campanulate* flowers with small star shaped calyx.
- *Natural flowering season.*—Continuous throughout the spring and summer. Season can be extended by vernalization and long day treatments.
- *Flower longevity on the plant.*—Longevity of individual flowers is highly dependent on temperature and light conditions. Flowers persistent.
- *Number of flowers per inflorescence.*—4–5.
- *Inflorescence size.*—Length: about 11 cm.

Flowers:
- *Length.*—About 20 mm.
- *Diameter.*—about 22 mm. Lanceolate, acuminate petal lobes: 10 mm long and 6 mm wide.
- *Corolla color.*—Upper and lower surfaces, N87B and C respectively, blue, also the bottom of the bell has this color.

Buds:
- *Length.*—Up to 15 mm, diameter: up to 4 mm, oblong, ridged shaped, color: white to N88B.

Petals:
- *Arrangement.*—single, sympetalous, campanulate; 5 in number, Basally fused, entire margin, acute apex, length: 8–10 mm, width: 7 mm, color when opening RHS N87D, color when fully opened: RHS N87B (upper side) and RHS N87C (under side); velvety texture.

Sepals:
- Shiny, glabrous, free arrangement, 5 in number, cuspidate apex, fused base, length: 3 mm, width: 1 mm, color: immature upper and under side RHS 144B; mature upper and under side RHS 138 A.

Peduncle:
- *Strength.*—Moderately strong.
- *Length.*—About 25 mm.
- *Diameter.*—About 1 mm.
- *Color.*—138D light green.

Reproductive organs:
- *Stamen.*—5, fused until pollen shed.
- *Anther.*—1 mm in size, color RHS 158 B.
- *Pollen.*—RHS 158 B, average production.
- *Pistil.*—1, 12 mm in length, conspicuous tripartite in shape.
- *Stigma.*—RHS 85A in color, conspicuous tripartite in shape.
- *Style.*—Length: 11 mm, color RHS 84B.
- *Ovary.*—RHS 150D.

Seed:
- *Length.*—About 1 mm.
- *Diameter.*—about 0.3 mm; quantity: 20–30 per flower.

Growth retardants: No growth retardants were used in the breeding program.

Weather tolerance: Plants of the new *Campanula* have exhibited good tolerance to drought, rain and wind, low temperature resistant to −20C.

We claim:

1. A new and distinct cultivar of *Campanula* plant named 'PKMp02', as illustrated and described herein.

* * * * *

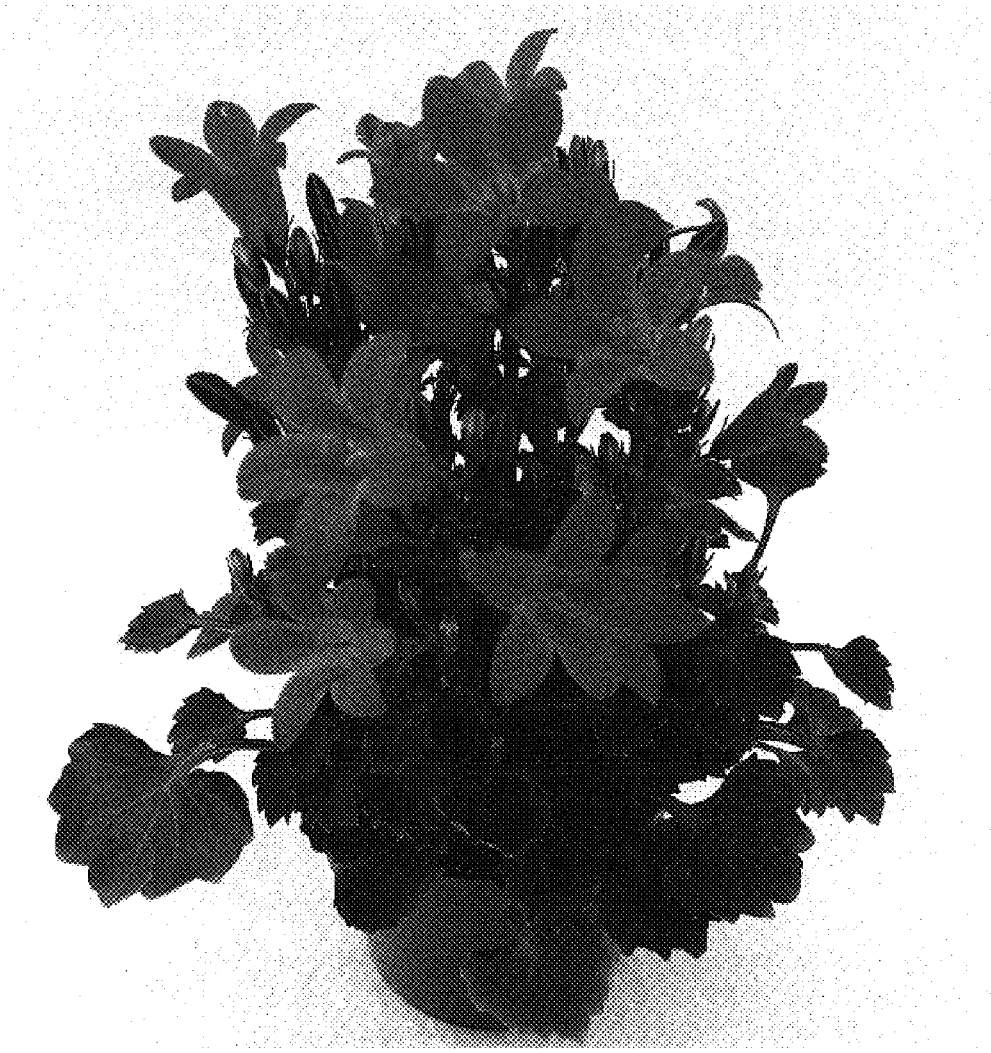

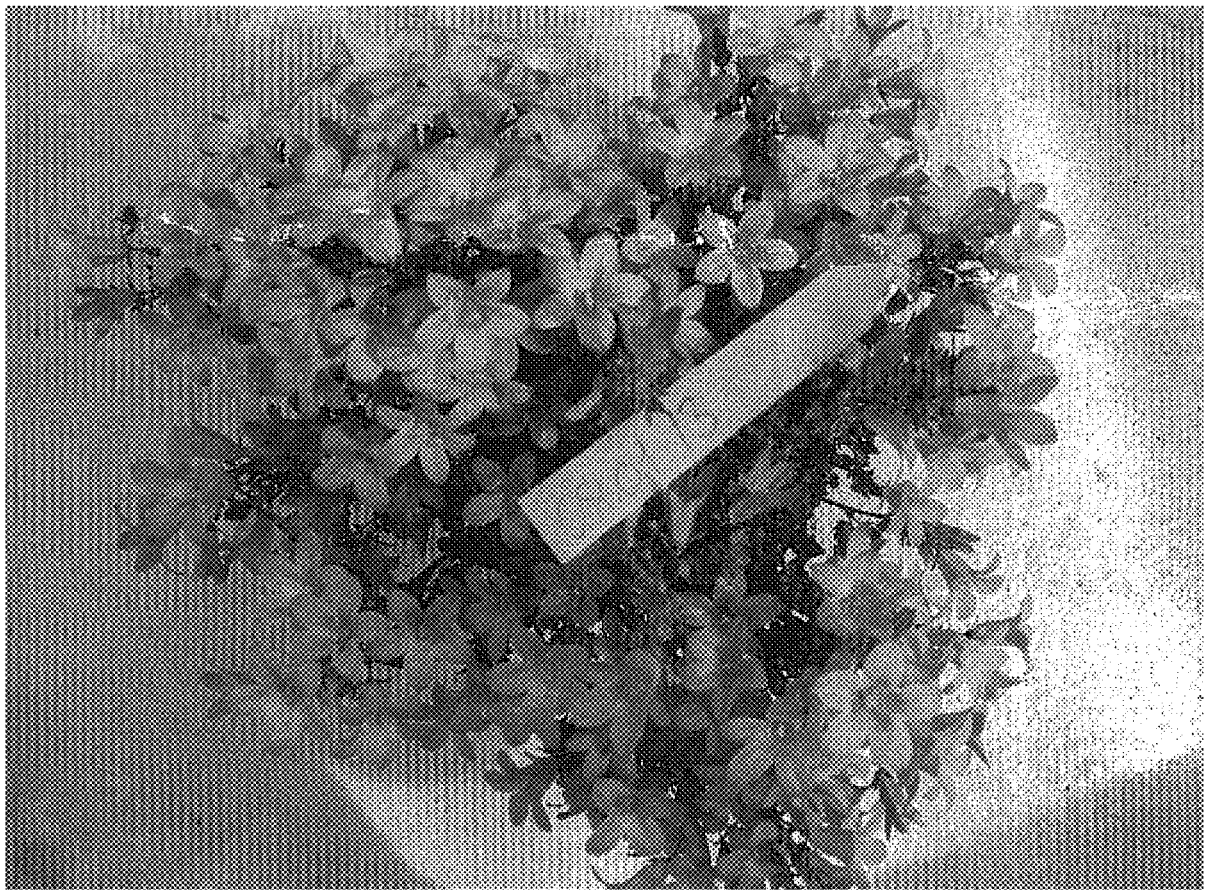

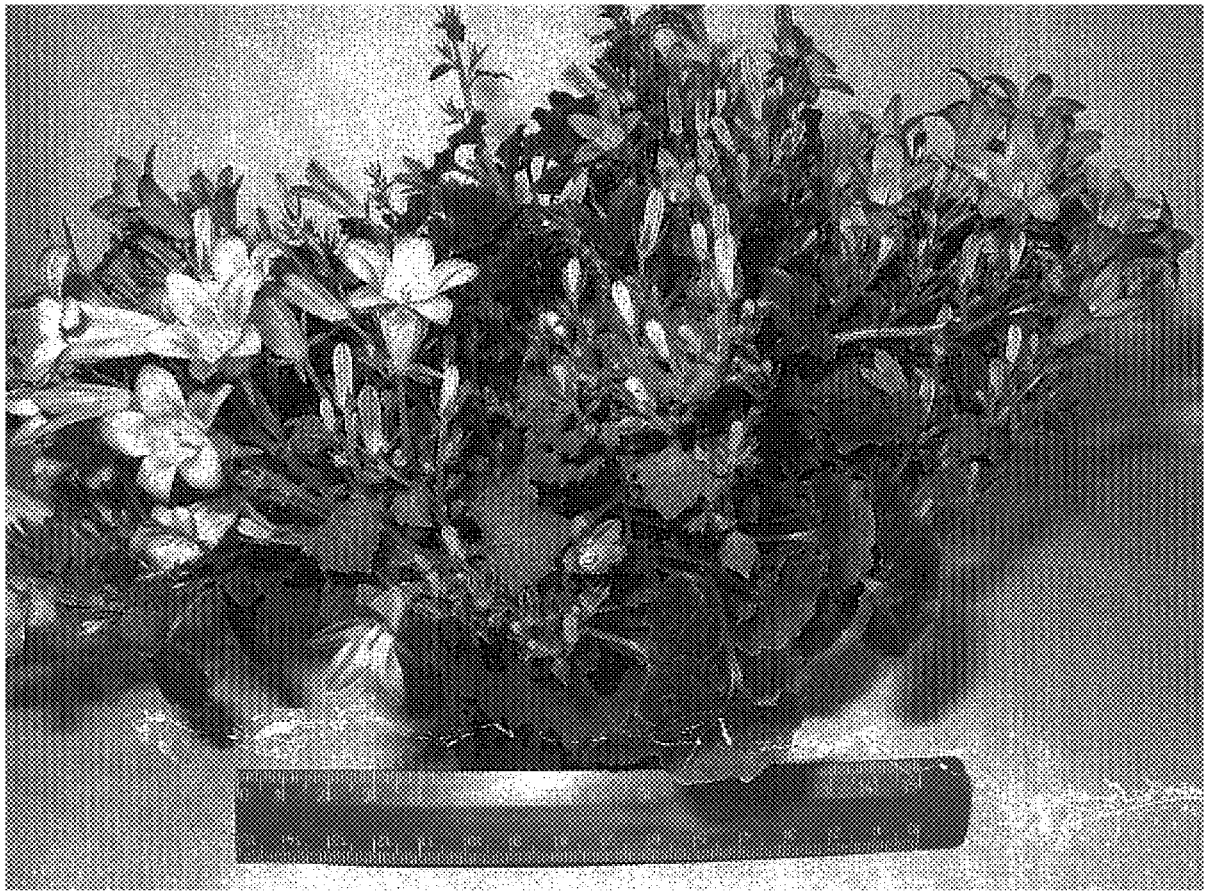

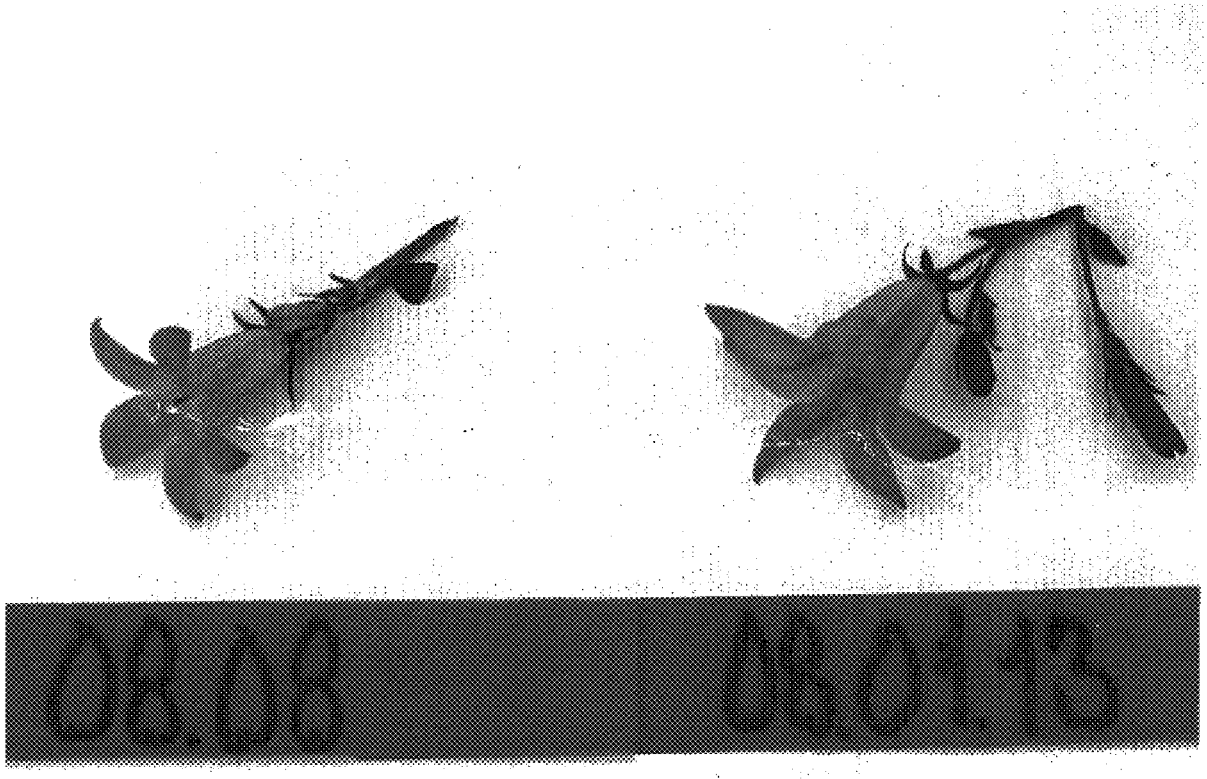
08.08
08.04.15